(12) United States Patent
Smith et al.

(10) Patent No.: US 6,536,428 B1
(45) Date of Patent: Mar. 25, 2003

(54) VENTILATION SYSTEM AND/OR BREATHING TUBE

(75) Inventors: Daniel John Smith, Auckland (NZ); Craig Karl White, Auckland (NZ)

(73) Assignee: Fisher & Paykel Limited, Auckland (NZ)

( * ) Notice: Subject to any disclaimer, the term of this patent is extended or adjusted under 35 U.S.C. 154(b) by 0 days.

(21) Appl. No.: 09/634,168

(22) Filed: Aug. 9, 2000

(30) Foreign Application Priority Data

Aug. 10, 1999 (NZ) ................................. 337174

(51) Int. Cl.$^7$ .............................................. A61M 16/00
(52) U.S. Cl. ............................... 128/203.17; 128/204.17
(58) Field of Search ....................... 128/203.12, 203.16, 128/203.17, 200.24, 203.24, 204.17, 204.18, 204.21, 207.14, 911, 912, 203.27, 203.22; 138/111–114, 121

(56) References Cited

U.S. PATENT DOCUMENTS

| | | | | |
|---|---|---|---|---|
| 3,856,051 A | * | 12/1974 | Bain | 128/203.12 |
| 3,865,106 A | | 2/1975 | Paluch | |
| 4,007,737 A | | 2/1977 | Paluch | |
| 4,214,147 A | * | 7/1980 | Kraver | 219/301 |
| 4,232,667 A | * | 11/1980 | Chalon et al. | 128/203.12 |
| 4,265,235 A | * | 5/1981 | Fukunaga | 128/200.24 |
| 4,265,239 A | * | 5/1981 | Fischer et al. | 128/205.17 |
| 4,462,397 A | | 7/1984 | Suzuki | |
| 4,463,755 A | | 8/1984 | Suzuki | |
| 4,637,384 A | | 1/1987 | Schroeder | |
| 4,676,239 A | * | 6/1987 | Humphrey | 128/203.28 |
| 4,686,354 A | * | 8/1987 | Makin | 128/204.17 |
| 4,967,744 A | | 11/1990 | Chua | |
| 5,121,746 A | * | 6/1992 | Sikora | 128/203.12 |
| 5,284,160 A | * | 2/1994 | Dryden | 128/203.12 |
| 5,357,948 A | * | 10/1994 | Eilentropp | 128/203.26 |
| 5,404,873 A | | 4/1995 | Leagre et al. | |
| 5,640,951 A | * | 6/1997 | Huddart et al. | 128/203.26 |
| 5,894,839 A | * | 4/1999 | Rosenkoetter et al. | 128/200.24 |
| 5,901,705 A | * | 5/1999 | Leagre | 128/207.14 |
| 5,983,896 A | * | 11/1999 | Fukunaga et al. | 128/207.14 |

* cited by examiner

*Primary Examiner*—Aaron J. Lewis
*Assistant Examiner*—Teena Mitchell
(74) *Attorney, Agent, or Firm*—Trexler, Bushnell, Giangiorgi, Blackstone & Marr, Ltd.

(57) ABSTRACT

A breathing tube for humidified gases ventilation system has an internal conduit and a surrounding conduit within which the internal conduit is disposed. A connector at one end of the internal conduit and the surrounding conduit has an inhalation gases port for connection to an inhalation gases supply port of a ventilator. A gases flow path leads from the inhalation gases port to the space between the internal conduit and the surrounding conduit. A spirally wound heater wire may be disposed between the internal conduit and the surrounding conduit with turns of the spirally wound wire passing around the internal conduit.

6 Claims, 3 Drawing Sheets

VENTILATION SYSTEM AND/OR BREATHING TUBE

BACKGROUND TO THE INVENTION

I) Field of the Invention

The present invention relates to ventilation systems and to the form and configuration of breathing tubes therefor.

II) Summary of the Prior Art

Administration of gases to patients from a ventilator via one or more breathing tubes is well known in the art. In particular it is well known to provide a pair of breathing tubes, being an inhalation and an exhalation tube which connects to a yoke connector at the patient. Furthermore it is known to provide a humidification device in the inhalation line, usually close to the ventilator, to provide the inhaled gases at elevated humidity levels.

These systems have the disadvantage that the pair of breathing tubes are bulky and inconvenient to work with.

More recently breathing tubes have been suggested in which the inhalation line is concentrically located within a larger tube, with the space between the inhalation tube and the larger tube forming the exhalation path. These are said to improve upon the earlier dual tube configuration by reducing the bulk and inconvenience and by providing counterflow heat exchange between the inhalation and exhalation gases. Examples of such circuits are shown in U.S. Pat. No. 3,865,106, U.S. Pat. No. 4,007,737, U.S. Pat. No. 4,462,397, U.S. Pat. No. 4,463,755, U.S. Pat. No. 4,637,384, U.S. Pat. No. 4,967,744 and U.S. Pat. No. 5,404,873.

These configurations have encountered problems with humidified gases as condensation forms on the inside of the wall of the outer tube (which wall is in contact on its outer side with the ambient air) and collects along the lower side of the tube. This poses a particular problem as the inner inhalation tube also tends to lie along the lower side of the larger exhalation tube and therefore in contact with the collected condensate. This has an adverse affect on the maintenance of the temperature of the inhalation gases in the inhalation tube. While some of the gases in the inhalation tube remain at appropriate temperatures, those adjacent the lower wall of the inhalation tube can become subject to significant temperature drop and subsequent condensation onto the tube or wall. It will be readily appreciated that formation of condensation makes it both difficult to control the operation of the humidifier to maintain comfortable levels of humidity at the patient and also can require the incorporation of devices which allow the egress of the condensation and ensure that such liquid does not reach the patient.

SUMMARY OF THE INVENTION

It is therefore an object of the present invention to provide a ventilation system and/or a breathing tube therefor which at least goes some way to overcoming the above disadvantages or which will at least provide the healthcare industry with a useful choice.

In a first aspect the invention consists in a humidified gases ventilation system comprising:

a patient interface means for connection with a patient and immediate delivery of gases thereto, a humidified ventilation means for providing a flow of pressurised and humidified gases, and a gases pathway connecting between said patient interface means and said humidified ventilation means and having an internal conduit and a surrounding conduit within which said internal conduit is disposed, said space between said internal conduit and said surrounding conduit connected with the inhalation port of said humidified ventilation means for supply of said humidified gases therethrough to said patient interface means.

In a still further aspect the invention consists in a breathing tube for a humidified gases ventilation system comprising:

an internal conduit, a surrounding conduit within which said internal conduit is disposed, and a connector at one end of said internal conduit and said surrounding conduit, said connector having an inhalation gases port for connection to the inhalation gases supply port of a ventilator, and a gases flow path from said inhalation gases port to said space between said internal conduit and said surrounding conduit.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

DETAILED DESCRIPTION

Figure 1:
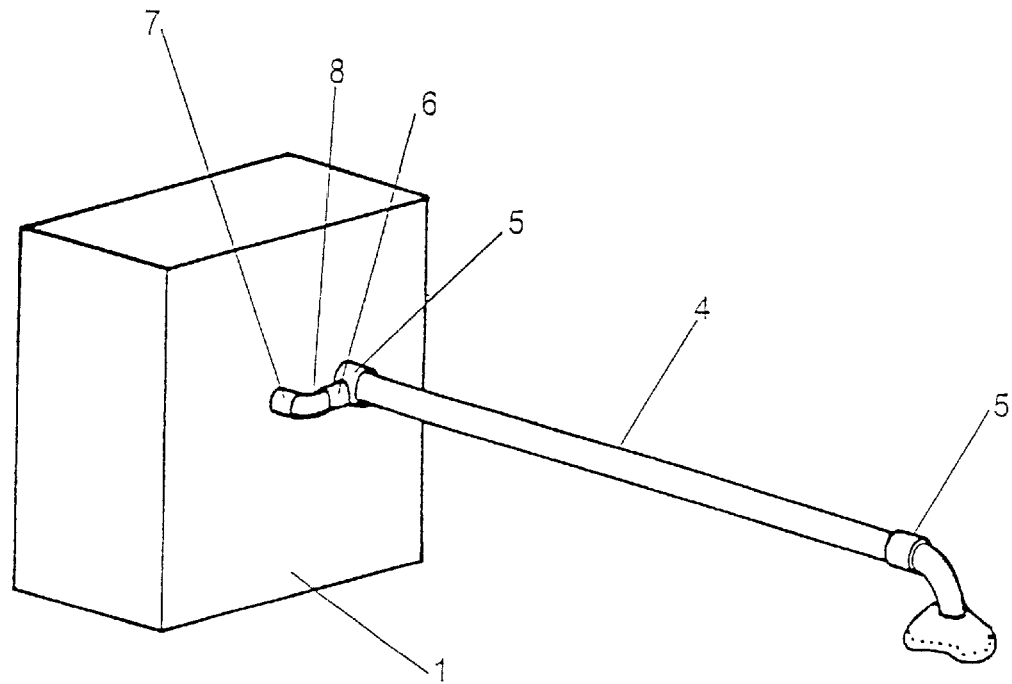
FIG. 1 shows a ventilation system according to the preferred embodiment of the present invention.
Figure 4:
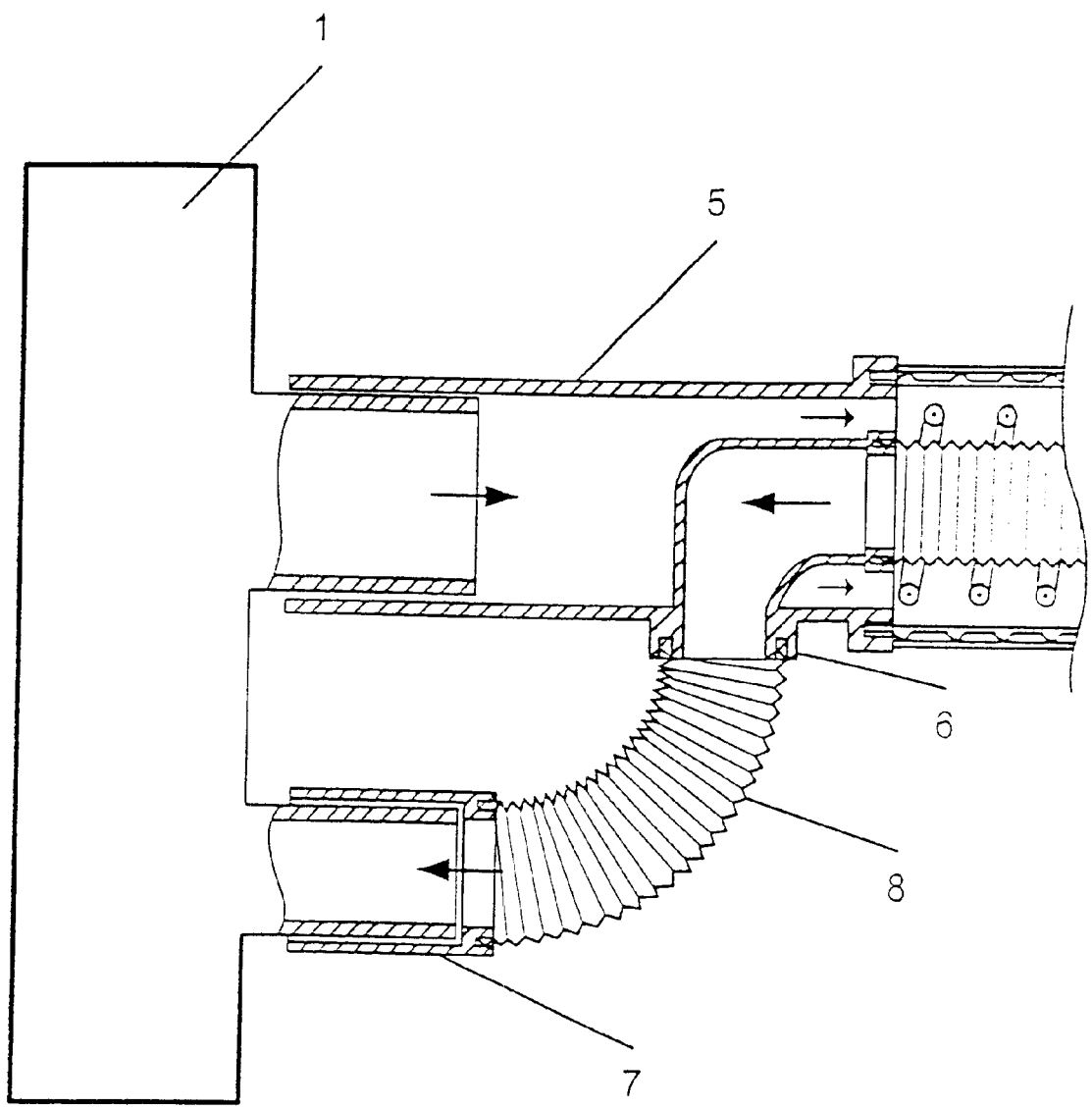
FIG. 4 is a cross sectional view of the connections between the ventilator and the breathing tube.

With reference to FIG. 1 and FIG. 4, the present invention provides for a ventilation system including a ventilator 1 connected to a patient interface via a single breathing tube 4 providing both the inhalation and exhalation paths. The breathing tube 4 connects to the patient interface via a connector 5 at the patient end thereof. This interface may be for example a breathing mask (shown) or intubation tube. At the ventilator end the breathing tube 4 will connect to the ventilator inhalation and exhalation ports generally by a pair of connectors 5, 7 as required to interface with existing ventilators. In this regard connector 5 includes a first port to interface directly with one of the inhalation or exhalation ports (preferably the exhalation port), while the second connector 7 is connected to a second port 6 of the connector 5 by a branch tube 8.

The ventilator 1 may in fact comprise a ventilator and an in line humidifier of known type in which case the inhalation connector of the breathing tube connects to the outlet port of the humidifier and the exhalation connector connects to the appropriate port on the ventilator. As with conventional systems the inhalation gases are passed from the ventilator to the humidifier before reaching the breathing tube leading to the patient.

With regard to the above description of the configuration of connectors, it will also be appreciated that appropriately configured ventilators could be constructed which interface more directly with a single connector of the breathing tube and the above description is given to show the manner in which the present invention is adaptable to the connection requirements of existing ventilators.

Various configurations of the connection and connectors at both ends of the breathing tube are possible depending on the devices required to be interfaced with, and importance is only placed on the requirement that the connection be configured such that inhalation gases pass through the space between the surrounding tube 10 and the inner tube 11 (see FIG. 2) and exhalation gases pass through the inside of the inner tube 11.

Figure 2:
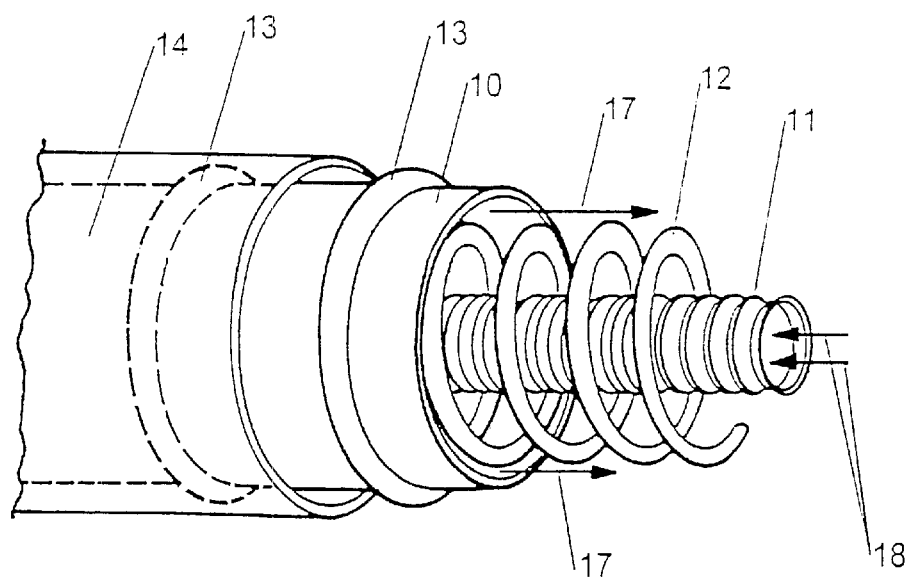
FIG. 2 is a cut-a-way view of the breathing tube according to the preferred embodiment of the present invention.
Figure 3:
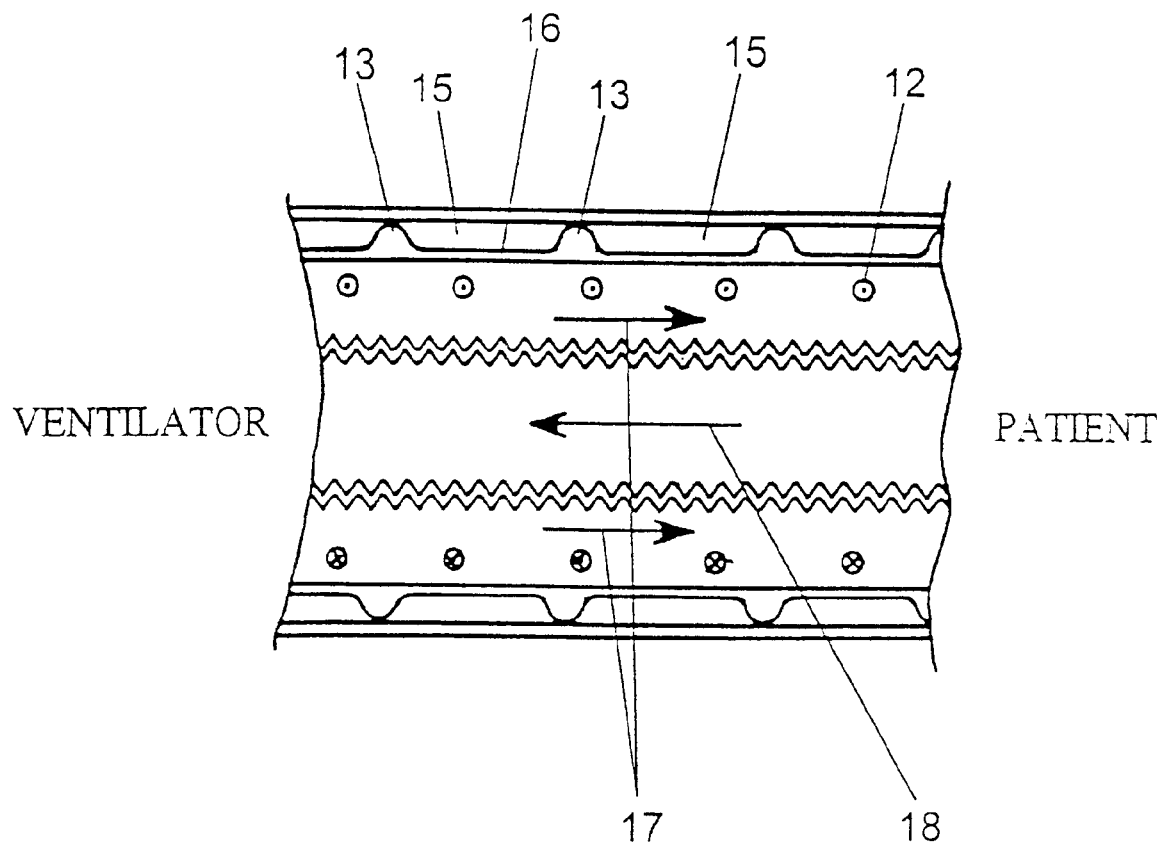
FIG. 3 is a cross sectional view of the section of the breathing tube according to FIG. 2.

Referring now specifically to FIGS. 2 and 3, the preferred form of the breathing tube is depicted. In this preferred form the breathing tube broadly comprises an inner tube 11 disposed within a surrounding tube 10. A spirally wound heating wire is located in the space between the inner tube 11 and the surrounding tube 10. The heater wire 12 spirals around the inner tube 11 but preferably is not in intimate contact therewith, rather being provided generally within that space. It is possible that the heater wire 12 may be imbedded in the wall of the surrounding tube 10, for example, by forming the surrounding tube 10 over the heater wire 12 provided on a former.

The inner tube 11 is preferably a corrugated plastics tube, the form and manufacture of which is well known in the art. The heating wire 12 may be, for example, an electrical resistive heater wire covered with a thermoplastic insulating layer, and be formed spirally, for example, by winding on a former, raising to an elevated temperature above the plastic temperature of the thermoplastic and recooling to ambient temperature. The heater wire thus formed will retain its spiral configuration and may be stretched the length of the conduit within the space between the inner tube 11 and the surrounding tube 10. The heater wire 12 may further be formed to have a pitch between adjacent turns which varies in a preferred manner along the length of the conduit, for example, to have a higher turn per length density at the patient end than at the ventilator end.

It is possible to provide the heater wire as a straight or single looped wire lying within either the inner tube or in the space between the inner tube and the surrounding tube. However such an embodiment is considered substantially inferior to the aforementioned spirally wound configuration and does not realise the advantages that are associated with the spirally wound configuration.

The surrounding conduit 10 preferably comprises a tube having a smooth inner wall and an outer wall including a plurality of corrugations. The outer wall corrugations are preferably formed by the inclusion of a series of spaced apart circumferential ribs 13. A jacket or sheath 14, preferably being a thin plastic membrane, is provided around the surrounding tube 10 and sized to be in intimate contact therewith, such that the jacket 14, the outer surface 16 of the surrounding tube 10 between the ribs and the adjacent ribs 13 together form annular air spaces 15. The annular air spaces 15 are effectively dead spaces and provide significant additional insulation which complements the provision of the heating element 12 within the space between the inner tube 11 and the surrounding tube 10.

In one possible embodiment the spirally wound heater wire 12 may be embedded in the smooth inner wall of the surrounding conduit. This may be achieved by winding an extruded narrow web along a former of appropriate dimension on which an appropriately configured heater wire has been predisposed.

As previously described, the connectors 5, 6 and 7 of the breathing tube are all configured such that inhalation gases pass in the direction indicated by arrows 17 through the space between the inner tube 11 and the surrounding tube 10 to the patient, while exhalation gases are caused to pass as indicated by arrows 18 through the inner tube 11.

The present invention provides significant performance advantages with respect to the breathing tubes and systems set forth in the prior art. In particular, the provision of the inhalation gases through the space between the inner tube 11 and the surrounding tube 10, in conjunction with a heating element, ensures that the gases most closely in contact with the ambient temperature surrounding the breathing tube are maintained at the most appropriate and controlled temperature. In turn the accurate control of temperature of those gases ensures that the temperature of the inner tube 11 is maintained also at an optimal temperature which in turn maintains the optimal temperature of the exhalation gases lying in the inner tube 11. The provision of jacket 14 surrounding the inner tube 10, in conjunction with the ribs 13 (which also have the separate purpose of providing radial rigidity for the tube 10) provides additional insulation to the inhalation gases path. The smooth inner wall of the surrounding conduit 10 reduces the likelihood of condensation formation, and ensures that the inner tube 11 is supported away from the surrounding tube 10 by the turns of the heater element 12.

What is claimed is:

1. A humidified gases ventilation system comprising:

a patient interface means for connection with a patient and immediate delivery of gases thereto, a humidified ventilation means for providing a flow of pressurised and humidified gases, and a gases pathway connecting between said patient interface means and said humidified ventilation means and having an internal conduit and a surrounding conduit within which said internal conduit is disposed, a space between said internal conduit and said surrounding conduit connected with an inhalation port of said humidified ventilation means for supply of said humidified gases therethrough to said patient interface means.

2. A humidified gases ventilation system as claimed in claim 1 including:

a spirally wound heating wire within the space between said internal conduit and said surrounding conduit, said heating wire passing around said internal conduit.

3. A breathing tube for a humidified gases ventilation system comprising:

an internal conduit, a surrounding conduit within which said internal conduit is disposed, and a connector at one end of said internal conduit and said surrounding conduit, said connector having an inhalation gases port for connection to the inhalation gases supply port of a ventilator, and a gases flow path from said inhalation gases port to a space between said internal conduit and said surrounding conduit.

4. A breathing tube for a humidified gases ventilation system as claimed in claim 3 and further including:

a spirally wound heater wire disposed in the space between said internal conduit and said surrounding conduit, said spirally wound heater wire passing around said internal conduit.

5. A breathing tube for a humidified gases ventilator system comprising:
- an internal conduit,
- a surrounding conduit within which said internal conduit is disposed, and
- a connector at one end of said internal conduit and said surrounding conduit, said connector having an inhalation gases port for connection to the inhalation gases supply port of a ventilator, and a gases flow path from said inhalation gases port to a space between said internal conduit and said surrounding conduit,
- a spirally wound heater wire disposed in the space between said internal conduit and said surrounding conduit, said spirally wound heater wire passing around said internal conduit, wherein
- said surrounding conduit has an externally corrugated form and an insulating jacket is provided over said surrounding conduit spanning said corrugations to provide an insulating air space within valleys of said corrugations.

6. A breathing tube as claimed in claim 5 wherein said surrounding tube has a smooth inner wall and a plurality of spaced apart circumferential ribs on an outer wall of said surrounding tube, providing said corrugations.

* * * * *